(12) United States Patent
Natarajan et al.

(10) Patent No.: US 12,297,229 B2
(45) Date of Patent: *May 13, 2025

(54) METHODS FOR INCREASING THE CAPACITY OF PURIFICATION PROCESSES

(71) Applicant: EMD Millipore Corporation, Burlington, MA (US)

(72) Inventors: Venkatesh Natarajan, Arlington, MA (US); Herbert Lutz, Playa del Rey, CA (US); Bala Raghunath, Bangalore (IN)

(73) Assignee: EMD Millipore Corporation, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/259,489

(22) Filed: Jan. 28, 2019

(65) Prior Publication Data

US 2019/0153027 A1     May 23, 2019

Related U.S. Application Data (63) Continuation of application No. 14/736,596, filed on Jun. 11, 2015, now Pat. No. 10,550,148.

(60) Provisional application No. 62/012,788, filed on Jun. 16, 2014.

(51) Int. Cl.
| | |
|---|---|
| *C07K 1/34* | (2006.01) |
| *B01D 15/08* | (2006.01) |
| *B01D 15/12* | (2006.01) |
| *B01D 61/14* | (2006.01) |
| *C07K 1/18* | (2006.01) |
| *C07K 1/22* | (2006.01) |
| *C07K 1/36* | (2006.01) |
| *C07K 16/00* | (2006.01) |
| *C07K 16/06* | (2006.01) |
| *A61L 2/00* | (2006.01) |

(52) U.S. Cl.
CPC ............. *C07K 1/18* (2013.01); *B01D 15/08* (2013.01); *B01D 15/12* (2013.01); *B01D 61/145* (2013.01); *C07K 1/22* (2013.01); *C07K 1/34* (2013.01); *C07K 1/36* (2013.01); *C07K 16/00* (2013.01); *C07K 16/065* (2013.01); *A61L 2/0017* (2013.01); *B01D 2311/08* (2013.01); *B01D 2313/58* (2013.01); *B01D 2315/10* (2013.01); *B01D 2315/16* (2013.01); *C07K 2317/14* (2013.01)

(58) Field of Classification Search
CPC ... C07K 1/18; C07K 1/22; C07K 1/34; C07K 1/36; C07K 16/00; C07K 16/065; C07K 2317/14; B01D 15/08; B01D 15/12; B01D 61/145; B01D 2311/08; B01D 2313/58; B01D 2315/10; B01D 2315/16; A61L 2/0017

See application file for complete search history.

(56) References Cited

U.S. PATENT DOCUMENTS

| | | | |
|---|---|---|---|
| 3,540,595 | A | 11/1970 | Edwards |
| 3,926,811 | A | 12/1975 | Ramsteck |
| 3,931,014 | A | 1/1976 | Heimbach et al. |
| 4,028,250 | A | 6/1977 | Loft |
| 4,222,874 | A | 9/1980 | Connelly |
| 4,756,835 | A | 7/1988 | Wilson |
| 4,765,906 | A | 8/1988 | Downing et al. |
| 4,956,085 | A | 9/1990 | Kopf |
| D325,070 | S | 3/1992 | Kopf |
| 5,114,582 | A | 5/1992 | Sandstrom et al. |
| D327,313 | S | 6/1992 | Kopf |
| 5,147,542 | A | 9/1992 | Proulx |
| 5,310,688 | A * | 5/1994 | Zale .............. B01D 15/3809 210/500.21 |
| D357,059 | S | 4/1995 | Kopf |
| 5,470,468 | A | 11/1995 | Colby |
| 5,538,642 | A | 7/1996 | Solie |
| 5,599,447 | A | 2/1997 | Pearl et al. |
| 5,654,025 | A | 8/1997 | Raghunath |
| 5,685,990 | A | 11/1997 | Saugmann et al. |
| 6,139,746 | A | 10/2000 | Kopf |
| 6,294,090 | B1 | 9/2001 | Nussbaumer et al. |
| 6,362,395 | B1 | 3/2002 | Poovaiah et al. |
| 6,365,395 | B1 | 4/2002 | Chris |
| 6,375,848 | B1 | 4/2002 | Cote et al. |

(Continued)

FOREIGN PATENT DOCUMENTS

| | | |
|---|---|---|
| CN | 1054379 A | 9/1991 |
| CN | 1274298 A | 11/2000 |

(Continued)

OTHER PUBLICATIONS

Dizon-Maspat, Biotechnology and Bioengineering, vol. 109, No. 4, Apr. 2012 (Year: 2012).*

(Continued)

*Primary Examiner* — Catherine S Hibbert
(74) *Attorney, Agent, or Firm* — EMD Millipore Corporation (57) ABSTRACT

In various embodiments, the present invention provides a process for separating target proteins from non-target proteins in a sample comprising increasing the concentration of the target proteins and non-target proteins in the sample and subsequently delivering the concentrated sample to a chromatography device. In other embodiments, the invention relates to a process for increasing the capacity of a chromatography device for a target protein by delivering a concentrated sample comprising the target protein to a chromatography device.

7 Claims, 4 Drawing Sheets

(56) References Cited

U.S. PATENT DOCUMENTS

| | | |
|---|---|---|
| 6,387,270 B1 | 5/2002 | van Reis |
| 6,402,956 B1 | 6/2002 | Andou et al. |
| 6,596,172 B1 | 7/2003 | Kopf |
| 6,926,833 B2 | 8/2005 | van Reis |
| 7,101,561 B2 | 9/2006 | Maertens et al. |
| 7,384,549 B2 | 6/2008 | de los Reyes et al. |
| 7,531,632 B2 | 5/2009 | Perreault |
| 7,682,511 B2 | 3/2010 | de los Reyes et al. |
| 7,959,805 B2 | 6/2011 | Chisolm et al. |
| 7,967,987 B2 | 6/2011 | de los Reyes et al. |
| D651,280 S | 12/2011 | Okawa et al. |
| D655,779 S | 3/2012 | Honda et al. |
| D655,780 S | 3/2012 | Honda et al. |
| 8,157,999 B2 | 4/2012 | de los Reyes et al. |
| 8,231,787 B2 | 7/2012 | Mir et al. |
| 8,506,802 B1 | 8/2013 | de los Reyes |
| 8,728,315 B2 | 5/2014 | de los Reyes et al. |
| 8,747,669 B1 | 6/2014 | Bonner et al. |
| D711,500 S | 8/2014 | Marchetti |
| 8,991,027 B2 | 3/2015 | Jons et al. |
| D729,897 S | 5/2015 | Ledbetter et al. |
| 9,133,433 B2 | 9/2015 | Vogel et al. |
| D741,983 S | 10/2015 | Mueller et al. |
| D761,381 S | 7/2016 | Natale et al. |
| D762,811 S | 8/2016 | Natale et al. |
| D811,519 S | 2/2018 | Natale et al. |
| 10,195,550 B2 | 2/2019 | Steen et al. |
| 10,207,225 B2 | 2/2019 | Lutz et al. |
| 10,350,518 B2 | 7/2019 | Steen et al. |
| D857,839 S | 8/2019 | Natale et al. |
| 10,399,039 B2 | 9/2019 | Steen |
| 10,550,148 B2 * | 2/2020 | Natarajan .............. C07K 16/00 |
| D912,765 S | 3/2021 | Natale et al. |
| 11,033,839 B2 | 6/2021 | Steen et al. |
| 11,033,939 B2 | 6/2021 | Hengen |
| 11,040,310 B2 | 6/2021 | Lutz et al. |
| 11,278,827 B2 | 3/2022 | Steen et al. |
| 11,617,988 B2 | 4/2023 | Lutz et al. |
| 11,679,349 B2 | 6/2023 | Steen et al. |
| 11,986,772 B2 | 5/2024 | Steen |
| 2002/0170859 A1 * | 11/2002 | Kopf ....................... C07K 1/18 210/659 |
| 2002/0177693 A1 | 11/2002 | Lebing et al. |
| 2003/0066794 A1 | 4/2003 | Diel |
| 2003/0111402 A1 | 6/2003 | Baig et al. |
| 2004/0167320 A1 | 8/2004 | Couto et al. |
| 2005/0184008 A1 | 8/2005 | Schacht |
| 2005/0197496 A1 | 9/2005 | Perreault |
| 2005/0218057 A1 | 10/2005 | Ngee |
| 2006/0051347 A1 | 3/2006 | Winter |
| 2006/0144788 A1 | 7/2006 | Cath et al. |
| 2006/0219635 A1 | 10/2006 | Mccague et al. |
| 2006/0292672 A1 | 12/2006 | Miller et al. |
| 2007/0138082 A1 | 6/2007 | Connors, Jr. et al. |
| 2007/0151924 A1 | 7/2007 | Mir et al. |
| 2007/0151925 A1 | 7/2007 | De et al. |
| 2007/0173638 A1 | 7/2007 | Buchacher et al. |
| 2007/0246406 A1 | 10/2007 | Dibel et al. |
| 2008/0087594 A1 | 4/2008 | Hermann et al. |
| 2008/0087595 A1 | 4/2008 | Hermann |
| 2008/0135500 A1 | 6/2008 | Gagnon et al. |
| 2008/0190836 A1 | 8/2008 | Beppu et al. |
| 2008/0202242 A1 | 8/2008 | Mickols et al. |
| 2009/0145838 A1 | 6/2009 | Knappe et al. |
| 2009/0214522 A1 | 8/2009 | Winter |
| 2009/0221047 A1 | 9/2009 | Schindler et al. |
| 2009/0266756 A1 | 10/2009 | Fischer-Fruehholz et al. |
| 2010/0006495 A1 | 1/2010 | Buschmann |
| 2010/0111378 A1 | 5/2010 | Kwan |
| 2010/0192976 A1 | 8/2010 | Lee et al. |
| 2011/0005984 A1 | 1/2011 | Boettcher et al. |
| 2011/0309018 A1 | 12/2011 | Kopf et al. |
| 2012/0316323 A1 | 2/2012 | Nardini et al. |
| 2012/0077963 A1 | 3/2012 | Hongo |
| 2012/0122076 A1 | 5/2012 | Lau et al. |
| 2012/0160758 A1 | 6/2012 | Beauchamp et al. |
| 2012/0166332 A1 | 6/2012 | Naaman |
| 2012/0168368 A1 | 7/2012 | De et al. |
| 2012/0264948 A1 | 10/2012 | Hilbert et al. |
| 2012/0298578 A1 | 11/2012 | Herrington et al. |
| 2013/0037486 A1 | 2/2013 | Sayer et al. |
| 2013/0098829 A1 | 4/2013 | Dontula et al. |
| 2013/0101797 A1 | 4/2013 | Dontula et al. |
| 2013/0146531 A1 | 6/2013 | Tayalia et al. |
| 2013/0334128 A1 | 12/2013 | Takagi et al. |
| 2014/0048483 A1 | 2/2014 | Maeda et al. |
| 2014/0130963 A1 | 5/2014 | Jons et al. |
| 2014/0231331 A1 | 8/2014 | de los Reyes et al. |
| 2014/0251896 A1 | 9/2014 | Hirozawa et al. |
| 2015/0093800 A1 | 4/2015 | Mahajan et al. |
| 2015/0144560 A1 | 5/2015 | Taniguchi et al. |
| 2015/0360180 A1 | 12/2015 | Lutz et al. |
| 2015/0361129 A1 | 12/2015 | Natarajan et al. |
| 2015/0375173 A1 | 12/2015 | Steen |
| 2016/0059159 A1 | 3/2016 | Steen et al. |
| 2016/0059160 A1 | 3/2016 | Steen et al. |
| 2016/0090514 A1 | 3/2016 | Wang et al. |
| 2017/0056825 A1 | 3/2017 | Schwan et al. |
| 2017/0157566 A1 | 6/2017 | Gefroh et al. |
| 2018/0078903 A1 | 3/2018 | Hillier |
| 2019/0099702 A1 | 4/2019 | Steen et al. |
| 2019/0099716 A1 | 4/2019 | Lutz et al. |
| 2019/0099717 A1 | 4/2019 | Lutz et al. |
| 2019/0134569 A1 | 5/2019 | Steen |
| 2019/0282937 A1 | 9/2019 | Steen et al. |
| 2019/0282963 A1 | 9/2019 | Steen |
| 2020/0246761 A1 | 8/2020 | Wohlleben et al. |
| 2020/0368646 A1 | 11/2020 | Salbaum et al. |
| 2021/0016520 A1 | 1/2021 | Mayes et al. |
| 2021/0123551 A1 | 4/2021 | Kuhn De Chizelle et al. |
| 2022/0176278 A1 | 6/2022 | Steen et al. |
| 2022/0212146 A1 | 7/2022 | Steen et al. |
| 2024/0050900 A1 | 2/2024 | Steen |

FOREIGN PATENT DOCUMENTS

| | | |
|---|---|---|
| CN | 103429308 | 12/2013 |
| CN | 105435504 A1 | 3/2016 |
| EP | 0 307 047 | 9/1988 |
| EP | 613 724 | 3/1989 |
| EP | 1 029 583 | 8/2000 |
| EP | 1 707 254 | 3/2006 |
| EP | 1 974 801 A2 | 1/2008 |
| EP | 2 067 522 | 5/2008 |
| EP | 1 944 076 A1 | 7/2008 |
| EP | 2 119 492 | 11/2009 |
| EP | 2 682 168 | 1/2014 |
| EP | 2 703 066 | 3/2014 |
| EP | 2 735 357 A1 | 5/2014 |
| EP | 2957336 A3 | 3/2016 |
| EP | 3527282 A1 | 8/2019 |
| JP | 54-149384 A | 11/1979 |
| JP | 55-109407 A | 8/1980 |
| JP | H01-159006 A | 6/1989 |
| JP | 5-51435 U | 7/1993 |
| JP | 2000288541 A | 10/2000 |
| JP | 2001252543 | 9/2001 |
| JP | 2006-247453 A | 9/2006 |
| JP | 2007-117949 A | 5/2007 |
| JP | 2008023415 | 2/2008 |
| JP | 2009178915 | 8/2009 |
| JP | 2010-053154 | 3/2010 |
| JP | 2013240765 | 5/2013 |
| JP | 5606615 B1 | 10/2014 |
| JP | 2015-9182 A | 1/2015 |
| JP | 2015-107467 A | 6/2015 |
| KR | 30-0646879 S | 5/2012 |
| KR | 2017-0135567 A | 12/2017 |
| WO | 91/11249 A1 | 8/1991 |
| WO | WO 2000/048703 | 8/2000 |
| WO | WO 2005/054287 | 6/2005 |
| WO | 2006/105555 A1 | 10/2006 |
| WO | WO 2007/076496 | 7/2007 |
| WO | WO 2007/076497 | 7/2007 |

(56) References Cited

FOREIGN PATENT DOCUMENTS

| WO | 2009/035700 A2 | 3/2009 | | |
|---|---|---|---|---|
| WO | WO 2009/064797 | 5/2009 | | |
| WO | WO 2011/094236 | 8/2011 | | |
| WO | WO 2012/039675 | 3/2012 | | |
| WO | 2012/091027 A1 | 7/2012 | | |
| WO | WO 2013/047744 | 4/2013 | | |
| WO | WO 2013/047746 | 4/2013 | | |
| WO | 2013/085755 A2 | 6/2013 | | |
| WO | WO 2013/106337 | 7/2013 | | |
| WO | WO 2013/125505 | 8/2013 | | |
| WO | WO 2014/067898 | 5/2014 | | |
| WO | WO-2014067898 A1 * | 5/2014 | ........... | B01D 15/363 |
| WO | WO 2015/133972 | 9/2015 | | |
| WO | 2015/195452 A2 | 12/2015 | | |
| WO | WO 2015/195453 | 12/2015 | | |
| WO | WO 2015/200691 A1 | 12/2015 | | |
| WO | WO2016/033546 | 3/2016 | | |
| WO | WO2016/033553 | 3/2016 | | |
| WO | 2017/213892 A1 | 12/2017 | | |

OTHER PUBLICATIONS

Ghose et al 2004 (Year: 2004).*
Written Opinion received for Singapore Application No. 10201504674T, mailed on Apr. 12, 2019.
Ushma Mehta at http://www.bioprocessintl.conn/2009/chronnasorb-single-use-membrane-based-anion-exchanger-206589/. (Year: 2009).
Hu, Journal of Chemical Engineering of Japan (2006), 39 (12); 1283-1290 (Year: 2006).
Casey et al., "Cadence Single-pass TFF Coupled with Chromatography Steps Enables Continuous Bioprocessing while Reducing Processing Times and Volumes," Retrieved from the internet: URL: www.pall.com/pdfs/Biopharmaceuticals/USD3003_Cadence_SPTFF_ChromSteps_AN.pdf, Retrieved on: Dec. 8, 2015, whole document.
Casey et al., "Protein concentration with single-pass tangential flow filtration (SPTFF)," *Journal of Membrane Science, 384(1)*: 82-88 (Sep. 2011).
Casey, C. et al., "CadenceTM Single-pass TFF Coupled with Chromatography Steps Enables Continuous BioProcessing while Reducing Processing Times and Volumes", Application Note (Jan. 2015).
Chinese Search Report for CN Application No. 201580000755.4, "Processes for Filtering Liquids Using Single Pass Tangential Flow Filtration Systems and Tangential Flow Filtration Systems With Recirculation of Retentate", Issued: Oct. 27, 2016.
Chinese Search Report for CN Application No. 201580000755.4, "Single Pass Tangential Flow Filtration Systems and Tangential Flow Filtration Systems With Recirculation of Retentate", Issued: Mar. 24, 2017.
Choo, K.-H. and C.-H. Lee, "Membrane fouling mechanisms in the membrane-coupled anaerobic bioreactor," Water Research, 30(8): 1771-1780 (Aug. 1996).
Dizon-Maspat, J. et al., "Single pass tangential flow filtration to debottleneck downstream processing for therapeutic antibody production," *Biotechnology and Bioengineering, 109(4)*: 962-970 (Apr. 2012).
Extended European Search Report for EP Application No. 15172144.6, titled: Single-Pass Filtration Systems And Processes, Dated: Nov. 20, 2015.
International Preliminary Report on Patentability for Int'l Application No. PCT/US2015/035251, Titled: "Methods for Increasing the Capacity of Flow Through Processes," Date Mailed: Dec. 20, 2016.
International Search Report and Written Opinion for International Application No. PCT/US2015/037780, "Compact Spiral-Wound Filter Elements, Modules and Systems", Date of Mailing: Sep. 7, 2015.
International Search Report and Written Opinion for Int'l Application No. PCT/US2015/035251, titled: Methods for Increasing the Capacity of Flow-Through Processes, Date Mailed: Dec. 18, 2015.

International Search Report and Written Opinion for Int'l Application No. PCT/US2015/035250, titled: Single-Pass Filtration Systems and Processes, Date Mailed: Dec. 14, 2015.
International Search Report and Written Opinion for Int'l Application No. PCT/US2015/047574, titled: Single Pass Tangential Flow Filtration Systems and Tangential Flow Filtration Systems With Recirculation of Retentate, Date Mailed: Dec. 7, 2015.
International Search Report and Written Opinion for Int'l Application No. PCT/US2015/047585, titled: Processes for Filtering Liquids Using Single Pass Tangential Flow Filtration Systems and Tangential Flow Filtration Systems With Recirculation of Retentate, Date Mailed: Dec. 7, 2015.
Internet blog, Tangential Flow Filtration http://blog.naver.com/amiconls/23855658 (Apr. 26, 2006).
Kwang-Ho, C. et al., "Membrane fouling mechanisms in the membrane-coupled anaerobic bioreactor," *Water Research, 30(8)*: 1771-1780 (Aug. 1996).
Liu, H.F., et al., "Recovery and purification process development for monoclonal antibody production," mAbs 2(5):480-499 (Sep. 1, 2010).
Lutz, H., *Ultrafiltration for Bioprocessing*, p. 93 (2015).
Maintenance Procedures PelliconTM and PelliconTM-2 Cassette Filters (Jul. 1998).
Merry, A.J., "Membrane equipment and plant design", *Industrial Membrane Separation Technology*, pp. 32-66 (1996).
Middlewood, P.G. et al., "Extraction of amaranth starch from an aqueous medium using microfiltration: Membrane fouling and cleaning," *Journal of Membrane Science, vol. 411- 412*, pp. 22-29 (Apr. 2012).
Notification Concerning Transmittal of Copy of International Preliminary Report on Patentability for International Application No. PCT/US2015/047574, "Single Pass Tangential Flow Filtration Systems and Tangential Flow Filtration Systems With Recirculation of Retentate", Date of Mailing: Mar. 9, 2017.
Notification Concerning Transmittal of Copy of International Preliminary Report on Patentability for International Application No. PCT/US2015/035250, "Single-Pass Filtration Systems and Processes", Date of Mailing: Dec. 29, 2016.
Notification Concerning Transmittal of Copy of International Preliminary Report on Patentability for International Application No. PCT/US2015/035251, "Methods for Increasing the Capacity of Flow-Through Processes", Date of Mailing: Dec. 29, 2016.
Notification Concerning Transmittal of Copy of International Preliminary Report on Patentability for International Application No. PCT/US2015/047585, "Processes for Filtering Liquids Using Single Pass Tangential Flow Filtration Systems and Tangential Flow Filtration Systems With Recirculation of Retentate", Date of Mailing: Mar. 9, 2017.
Notification Concerning Transmittal of Copy of International Preliminary Report on Patentability for International Application No. PCT/US2015/037780, "Compact Spiral-Wound Filter Elements, Modules and Systems", Date of Mailing: Jan. 5, 2017.
Pall Corporation Brochure "Cadence™ Single-Pass Tangential Flow Filtration Modules and Systems", (2014).
Partial European Search Report for EP Application No. 15172146.1, titled: "Compact Spiral-Wound Filter Elements, Modules and Systems", Dated: Nov. 6, 2015.
Rathore, A.S. et al., "Recent Developments in Membrane-Based Separations in Biotechnology Processes: Review," *Preparative Biochemistry and Biotechnology, 41(4)*: 398-421 (Oct. 2011).
Schwartz, L., "Diafiltration for Desalting or Buffer Exchange," BioProcess International, pp. 43-49 (2003).
Singapore Search Report for SG Application No. 10201504670R, "Methodology for Increasing the Capacity of Flow-Through Processes", Issued: Nov. 16, 2017.
Steen et al., "Single Pass Tangential Flow Filtration", ACS mtg. poster, Anaheim, CA Mar. 2011.
Teske et al., "Inline Ultrafiltration," *Biotechnol. Prog., 26(4)*: 1068-1072 (Mar. 2010).
van Reis, R. et al., "Linear Scale Ultrafiltration," *Biotechnology and Bioengineering, 55(5)*: 737-746 (Sep. 1997).

(56) References Cited

OTHER PUBLICATIONS

Zou, Y., et al., "New Technologies for high concentration protein ultrafiltration: High Viscosity TFF Cassettes and Single-Pass TFF", Oct. 2014, EMD Millipore, 1 pg.
Non-Final Office Action dated Apr. 2, 2018 for U.S. Appl. No. 14/839,779, "Single Pass Tangential Flow Filtration Systems and Tangential Flow Filtration Systems With Recirculation of Retentate".
Office Action dated Jun. 4, 2018 for U.S. Appl. No. 14/736,596, "Methods for Increasing the Capacity of Flow-Through Processes".
Notice of Allowance dated Oct. 15, 2018 for U.S. Appl. No. 14/736,596, "Methods for Increasing the Capacity of Flow-Through Processes".
Notice of Allowance dated Oct. 24, 2018 for U.S. Appl. No. 14/839,779, "Single Pass Tangential Flow Filtration Systems and Tangential Flow Filtration Systems With Recirculation of Retentate".
Extended European Search Report received for European Patent Application No. 19163829.5, mailed on Jul. 24, 2019, 17 pages.
Extended European Search Report received for European Patent Application No. 20167074.2, mailed on Jun. 16, 2020, 18 pages.
International Search Report and Written Opinion for PCT Application No. PCT/US2017/034709 mailed on Aug. 3, 2017, 10 pages.
International Search Report and Written Opinion received for PCT Patent Application No. PCT/US2015/047585, mailed on Dec. 7, 2015, 9 pages.
Search Report received for Chinese Patent Application No. 201510335030.2, mailed on Jun. 26, 2017.
Pellicon, Available Online at: <https://www.emdmillipore.com/US/en/product/Pellicon-Single-Pass-TFF-Cassette-Retentate-Collection-Plate,MM_NF-XXSPTFF03>, 2020.
European Office Action received for Patent Application No. 17728414.8 mailed on Jan. 21, 2022, 4 pages.
European Office Action received for Patent Application No. 20167074.2 mailed on Mar. 25, 2022, 4 pages.
Non Final Office Action Received for U.S. Appl. No. 16/096,516, mailed on Jul. 21, 2022, 14 Pages.
Office Action received for Japanese Patent Application No. 2020-081059 mailed on Mar. 29, 2022, 6 Pages (3 Pages of English Translation & 3 Pages of Official Copy).
Appeal Decision received for U.S. Appl. No. 16/207,874, mailed on Jun. 1, 2022, 7 Pages.
Membrane operations, Separation Processes, Retrieved from Internet URL:<https://web.archive.org/web/20041113003913/http://www.separationprocesses.com/Membrane/MT_Chp05j.htm>, Nov. 13, 2004, pp. 1-2.
Notice of Allowance received for U.S. Appl. No. 16/207,874, mailed on Sep. 7, 2022, 5 Pages.
Non Final Office Action Received for U.S. Appl. No. 17/315,721 mailed on Oct. 14, 2022, 6 Pages.
Non Final Office Action Received for U.S. Appl. No. 17/656,285, mailed on Oct. 14, 2022, 15 Pages.
Extended European Search Report received for European Patent Application No. 22174654.8 mailed on Aug. 3, 2022, 12 Pages.
Extended European Search Report received for European Patent Application No. 22200930.0, mailed on Feb. 3, 2023, 11 Pages.
Notice of Allowance received for U.S. Appl. No. 16/207,874, mailed on Jan. 17, 2023, 5 Pages.
Office Action received for Singaporean Patent Application No. 10202006102U mailing date Jul. 3, 2023, 5 Pages.
Notice of Allowance received for U.S. Appl. No. 16/207,874, mailing date Feb. 27, 2023, 2 Pages.
Notice of Allowance received for U.S. Appl. No. 16/207,874, mailing date Jan. 17, 2023, 5 Pages.
Notice of Allowance received for U.S. Appl. No. 17/315,721, mailing date Feb. 17, 2023, 5 Pages.
Notice of Allowance received for U.S. Appl. No. 17/315,721, mailing date Mar. 2, 2023, 2 Pages.
Final Office Action Received for U.S. Appl. No. 17/656,285, mailing date Mar. 3, 2023, 17 Pages.
Notice of Allowance received for U.S. Appl. No. 17/656,285, mailing date Aug. 2, 2023, 9 Pages.
Office Action received for Japanese Patent Application No. 2022-120234 mailing date Sep. 5, 2023, 5 Pages (2 Page of English translation and 3 pages of official copy).
TFF system improves recovery and increases yield, Pall Corporation, Membrane Technology, vol. 2010, No. 5, May 2010, pp. 2-3.
Communication pursuant to Article 94(3) EPC received for European Patent Application No. 22195919.0 mailing date Dec. 6, 2023, 11 Pages.
Notice of Allowance received for U.S. Appl. No. 17/656,285, mailing date Feb. 21, 2024, 8 Pages.
Office Action received for Chinese Patent Application No. 202210363469.6 mailing date Mar. 30, 2024, 7 Pages (4 Pages of English Translation & 3 Pages of Official copy).
Office Action received for Chinese Patent Application No. 202211266108.6 mailing date Jan. 31, 2024, 16 Pages (9 Pages of English translation and 7 pages of official copy).
Office Action received for Chinese Patent Application No. 202211266108.6 mailing date May 7, 2024, 12 Pages (5 Pages of English Translation & 7 Pages of Official Copy).
Non-Final Office Action Received for U.S. Appl. No. 17/682,221, mailing date Aug. 14, 2024, 10 pages.
Decision of Rejection Received for Chinese Patent Application No. 202211266108.6, mailing date Aug. 30, 2024, 12 Pages (5 Pages of English translation and 7 pages of official copy).

* cited by examiner

METHODS FOR INCREASING THE CAPACITY OF PURIFICATION PROCESSES

RELATED APPLICATIONS

This application is a continuation of U.S. application Ser. No. 14/736,596, filed Jun. 11, 2015, which claims the benefit of U.S. Provisional Application No. 62/012,788, filed on Jun. 16, 2014. The entire teachings of the above applications are incorporated herein by reference.

BACKGROUND OF THE INVENTION

Process-scale applications for the purification of monoclonal antibodies (MAbs) or virus filtration typically utilize bind-and-elute processes, and flow-through processes, such as anion exchange (AEX) and hydrophobic interaction (HIC) chromatography processes, to remove host cell proteins (HCP) and other impurities from a liquid sample, or feed. Typically, the operating conditions for these flow-through processes are chosen such that the target proteins (e.g., MAbs) are not retained on the chromatography surface and, as a result, flow through the chromatography device. Typically, the operating conditions for bind-and-elute processes are chosen such that the target proteins (e.g., MAbs) are retained or bound on the chromatography surface and then recovered by an elution step, wherein the bound target protein is displaced from the chromatography surface and recovered.

For traditional AEX chromatography resins, it is often necessary to dilute the feed prior to loading the chromatography device to reduce solution conductivities to levels that promote the binding of impurities. The inconvenience and time commitment required for such feed dilution has provided the impetus to develop salt-tolerant functionalities that do not require feed dilution for efficient adsorption of impurities. While the capacities for traditional AEX membranes are typically in the range of about 100-200 g MAb/mL resin, corresponding capacities for salt-tolerant membrane adsorbers are greater and range, for example, from about 4-7 kg MAb/L resin. However, for a chromatography process to be economical at a process scale, the capacity of the chromatography resin should preferably be about 10-15 kg MAb/L membrane or greater.

Thus, there is a current need to develop methods for increasing the capacity of existing chromatography resins and devices to levels that would render flow-through processes, bind-and-elute processes, and simulated flow-through processes more economical at a process scale.

SUMMARY OF THE INVENTION

The present invention provides, in one embodiment, a process for separating target proteins from non-target proteins in a liquid sample, comprising obtaining a liquid sample containing target proteins and non-target proteins; increasing the concentration of the target proteins and non-target proteins in the sample to produce a concentrated feed for delivery to a chromatography device; delivering the concentrated feed to the chromatography device; separating the target proteins from the non-target proteins in the chromatography device; and recovering the target proteins from the chromatography device. In a particular embodiment, the target proteins are monoclonal antibodies (MAbs).

In another embodiment, the invention relates to a process for increasing the capacity of a chromatography device for a target protein, comprising obtaining a liquid sample containing target proteins and non-target proteins; increasing the concentration of the target proteins and non-target proteins in the sample to produce a concentrated feed for delivery to a chromatography device; and delivering the concentrated feed to the chromatography device, wherein the capacity of the chromatography device for the target protein is increased. In a particular embodiment, the target proteins are monoclonal antibodies (MAbs).

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

The present invention provides, in one embodiment, a process for separating target proteins from non-target proteins in a liquid sample. In another embodiment, the invention relates to a process for increasing the capacity of a chromatography device for a target protein. These processes are referred to collectively herein as processes of the invention.

Without wishing to be bound by any one particular theory, it is believed that increasing the concentration of both target and non-target proteins in a feed sample prior to delivery to a chromatography device will increase the capacity of the device for the target protein. As used herein, "increasing the capacity of a chromatography device" means increasing the mass loading per volume of media in the device. Preferably, the processes described herein can increase the capacity of a chromatography device to a range of at least about 10 to about 15 kg target protein/L chromatography media, or greater.

The processes of the invention generally can comprise the steps of obtaining a liquid sample containing target proteins and non-target proteins; increasing the concentration of the target proteins and non-target proteins in the sample to produce a concentrated feed for delivery to a chromatography device; and delivering the concentrated feed to the chromatography device. In some embodiments, the processes of the invention can also include the steps of separating the target proteins from the non-target proteins in the chromatography device and recovering the target proteins from the chromatography device.

The liquid sample, also referred to herein as a "liquid feed" or "feed sample," can be any liquid that contains a target protein of interest (e.g., MAbs) and one or more impurities (e.g., non-target proteins). Typically, the liquid sample is obtained from a source of the target protein (e.g., a hybridoma or other host cell expressing a MAb). In a particular embodiment, the target protein in the liquid sample is a monoclonal antibody (MAb) and the non-target proteins are host cell proteins (HCPs) (e.g., proteins from host hybridoma cells). Non-target proteins are generally a heterogeneous mixture of proteins of varying sizes, hydrophobicities and charge densities.

The processes of the invention include the step of increasing the concentration of the target proteins and non-target proteins in the sample to produce a concentrated feed for delivery to a chromatography device. Concentration of the sample will generally increase the concentration of both the target protein and non-target proteins in the sample. The overall protein concentration can be increased, for example, about 1.5×, 2×, 2.5×, 5× or 10× prior to loading onto a chromatography device compared to a liquid feed that has not been subjected to a concentration step prior to loading onto a chromatography device. In certain embodiments, the concentration may be increased more than 10×, provided that the target and non-target proteins remain soluble.

A variety of methods and techniques for increasing the concentration of proteins in a sample are well known to those of ordinary skill in the art to which this invention pertains. Such methods include, but are not limited to, tangential flow filtration (TFF) processes (e.g., TFF ultrafiltration), ultrafiltration processes using centrifugal filters, ultrafiltration processes using stirred cells, lyophilization, evaporation, precipitation, crystallization, aqueous two-phase separation and dialysis. In a particular embodiment, the concentration of the target proteins and non-target proteins in the sample is increased using a tangential flow filtration (TFF) process. The TFF process can be a recirculation TFF process, a single-pass TFF (SPTFF) process where the retentate and permeate are recovered from the system in separate containers without recirculation through the TFF system, or a TFF process operated in single-pass TFF mode where the permeate and a portion of the retentate from the system are recovered in separate containers without recirculation through the TFF system, and the remainder of the retentate is recirculated through the TFF system at least once. The retentate that is being recirculated can be returned to any upstream location in or before the TFF system. In one embodiment, the retentate is recirculated to the feed tank. In another embodiment, the retentate is recirculated to the feed line near the feed pump before the feed inlet on the TFF system. "Single-pass TFF mode" refers to operating conditions for a TFF system under which all or a portion of the retentate is not recirculated through the system. Preferably, the TFF process is a SPTFF process.

TFF processes are well known. TFF is a separation process that uses membranes to separate components in a liquid solution or suspension on the basis of size, molecular weight or other differences. In traditional TFF processes, the fluid is pumped tangentially along the membrane surface and particles or molecules which are too large to pass through the membrane are rejected and returned to a process tank for additional passes across the membrane (e.g., recirculation) until the process fluid is sufficiently concentrated or purified. The cross-flow nature of TFF minimizes membrane fouling, thus permitting high volume processing per batch. Single-Pass TFF (SPTFF) allows direct flow-through concentration of a product (e.g., protein) in the absence of recirculation, which reduces overall system size and permits continuous operation at high conversion levels.

TFF processes can further comprise performing diafiltration (e.g., to remove or lower the concentration of salts or solvents in the liquid feed, or to accomplish buffer exchange). In a preferred embodiment, the diafiltration is performed by concentrating the liquid feed (e.g., by TFF) to reduce the diafiltration volume and then restoring the feed to its starting volume by adding diafiltration solution (e.g., diafiltration buffer), a process which is known in the art as discontinuous, or batch, diafiltration. In another embodiment, the diafiltration is performed by adding the diafiltrate solution to retentate to increase the diafiltration volume followed by concentrating the sample to restore it to its original volume. In yet another embodiment, the diafiltration is performed by adding the diafiltration solution to unfiltered feed at the same rate that permeate is removed from the TFF system, a process which is known in the art as continuous, or constant-volume, diafiltration. Suitable diafiltration solutions are well known and include, for example, water and various aqueous buffer solutions.

Suitable TFF systems capable of being used in TFF processes are well known in the art to which the present invention pertains and include, but are not limited to, those described in U.S. Pat. No. 5,147,542, the contents of which are incorporated herein by reference in their entirety, and commercially available TFF systems from EMD Millipore Corporation (Billerica, MA) including, for example, LAB-SCALE™ TFF Systems, COGENT® M1 TFF Systems, COGENT® uScale TFF Systems, FLEXWARE® Assemblies for TFF, PROFLUX® TFF Systems, and PROSTAK™ TFF Systems.

In certain embodiments, the sample is diluted to produce a diluted feed (e.g., to lower the conductivity of the sample) prior to increasing the concentration of the target proteins and non-target proteins in the sample. Such a feed dilution step is particularly desirable when using a chromatography device that contains a standard AEX medium that lacks a salt-tolerant membrane adsorber. The dilution can be performed in-line with a subsequent concentration of the sample (e.g., by SPTFF) prior to loading the concentrated sample onto the chromatography device. Typically, a sample will be diluted 2-3× for most ion exchange applications.

The processes of the invention include the step of delivering a concentrated feed to a chromatography device. Suitable chromatography devices for use in the processes of the invention are well known in the art. Exemplary chromatography devices include, but are not limited to, membrane adsorbers, such as CHROMASORB™ devices, MOBIUS® FlexReady Solution, ISOPAK® Columns, HIBAR® Columns, RoboColumns and MiniChrom columns, K-PRIME® Systems, VANTAGE® Columns, and QUIKSCALER Columns, all of which are available commercially from EMD Millipore Corporation (Billerica, MA).

Typically, a chromatography device (e.g., a chromatography column, a chromatography cartridge) will be selected based on the chromatography medium. A person of ordinary skill in the art can readily determine a chromatography medium that is suitable for separation/purification of a particular target protein. Typical separation media (e.g., chromatography resins, chromatography beads, chromatography membranes, chromatography fibers) include, but are not limited to, anion-exchange (AEX) chromatography media, hydrophobic interaction chromatography (HIC) media, size-exclusion chromatography media, cation-exchange chromatography (CEX) media, affinity chromatography media (protein A affinity media, protein G affinity media, immobilized metal ion affinity media) and mixed-mode media.

In a particular embodiment, the chromatography device includes an anion-exchange (AEX) chromatography medium. Suitable AEX chromatography devices for use in the processes described herein include, for example, CHROMASORB™ devices available from EMD Millipore Corporation (Billerica, MA). An exemplary AEC medium for a chromatography device is ESHMUNO® Q Resin (EMD Millipore Corporation, Billerica, MA).

In another embodiment, the chromatography device includes a hydrophobic interaction chromatography (HIC) medium. Exemplary HIC media includes, e.g., FRACTOGEL® EMD Propyl and Phenyl resins (EMD Millipore Corporation).

In yet another embodiment, the chromatography device used in the processes of the invention includes a size-exclusion chromatography medium. An exemplary size-exclusion medium for a chromatography device FRACTOGEL® EMD BioSEC Media (EMD Millipore Corporation, Billerica, MA)

The need for sample dilution to lower conductivity for ion exchange chromatography using traditional ion exchange resins has led to the development of chromatography media having salt-tolerant functionalities that provide robust impurity removal over a wider conductivity range. The use of such salt-tolerant functionalities allows for the efficient adsorption of impurities without requiring dilution of the sample. Accordingly, in another embodiment, the chromatography device used in the processes of the invention can include a salt-tolerant membrane adsorber (e.g., a CHROMASORB™ Membrane Adsorber, available from EMD Millipore Corporation).

Preferably, the chromatography device used in the processes of the invention is disposable (e.g., a single-use chromatography device). Exemplary disposable chromatography devices include, for example, CHROMASORB™ devices, available from EMD Millipore Corporation).

Example 1: Concentrating a liquid feed sample containing target MAbs and host cell proteins prior to chromatographic separation increases processing capacity A cation exchange (CEX) (ESHMUNO® S Resin, EMD Millipore Corporation, Billerica, MA) elution pool of a target monoclonal antibody (MAb04) was divided into two aliquots. Aliquot 1 had a MAb04 concentration of 3.6 g/L. Aliquot 2 was concentrated using a CENTRIPREP® 30K centrifugal filter device (30 kDA Regenerated cellulose membrane) to yield a MAb04 concentration of ~5.8 g/L. The host cell protein (HCP) concentrations in the two feed streams were ~600 ng/ml in Aliquot 1 and ~820 ng/ml in Aliquot 2. The HCP levels in the filtrate in the CENTRIPREP® device were below the level of detection. The increase in HCP levels was not the same as the increase in the MAb concentration. This is most probably a reflection of the variability and sensitivity of the HCP ELISA assay. In addition, the use of ultrafiltration could also cause removal of HCP species (e.g., based on size). This may have a beneficial effect on capacity.

Each of the aliquots was then processed using a single-use membrane-based anion exchange (AEX) chromatography device (0.08 ml CHROMASORB™ Device, EMD Millipore Corporation).

Figure 1:
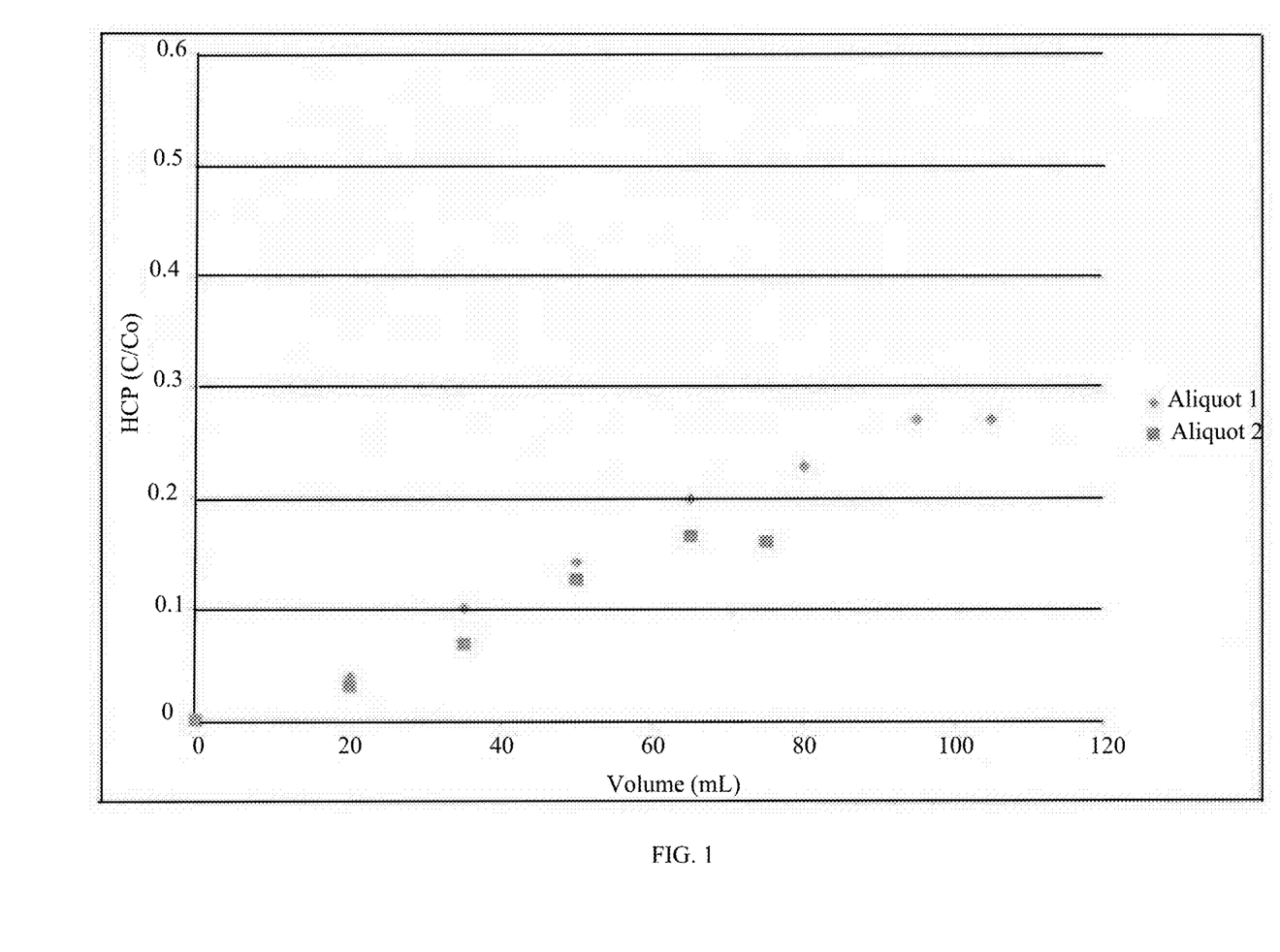
FIG. 1 is a graph showing host cell protein (HCP) breakthrough for two feed streams as a function of volume loaded. Aliquot 2 was approximately 1.5× more concentrated than Aliquot 1.
Figure 2:
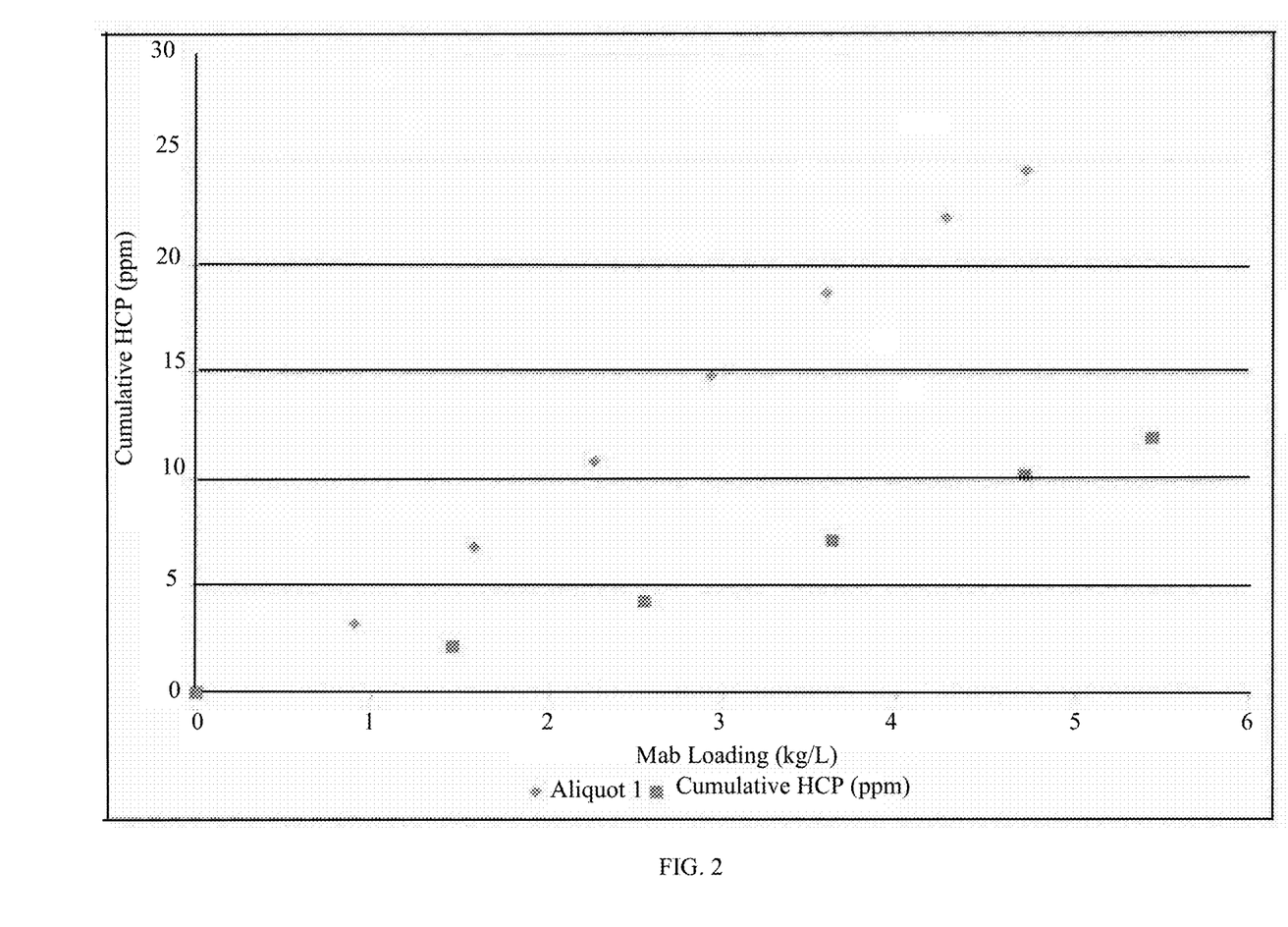
FIG. 2 is a graph showing a breakthrough curve of HCP removal as a function of MAb loading.

The breakthrough curves at the two concentrations are very similar, as expected for linear isotherms (FIG. 1). FIG. 2 illustrates the cumulative HCP (ppm) as a function of MAb loading. This type of graph is typically generated to identify the loading on the AEX device. The typical HCP target for AEX process is 10-20 ppm. For a 10 ppm target, the loading with Aliquot 1 would be restricted to 2 kg/L. However, with the more concentrated feed in Aliquot 2, the loading capacity increases to 4 kg/L.

Figure 3:
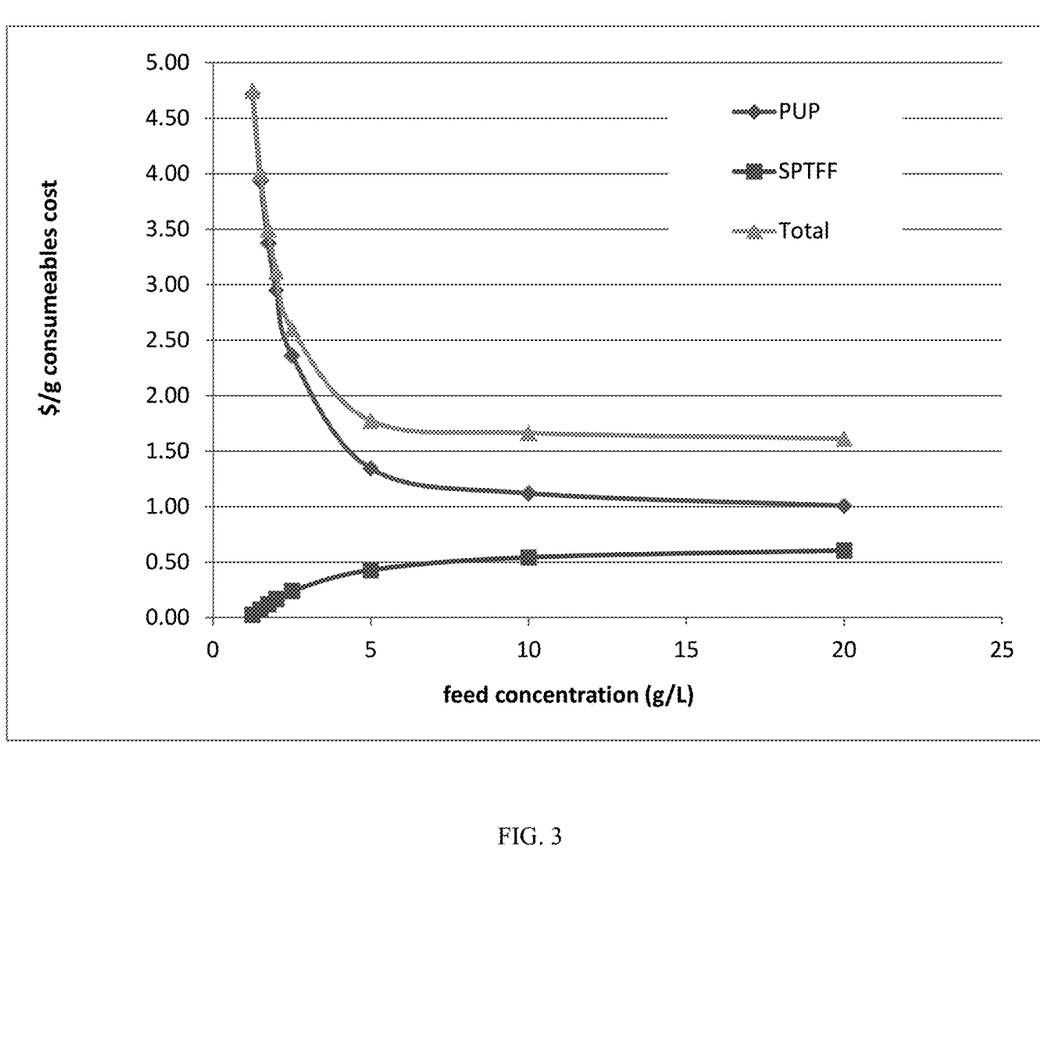
FIG. 3 is a graph plotting feed concentration in g/L against the cost of separation media in U.S. dollars/gram of media.

Example 2: Concentrating a Liquid Feed Prior to Protein a Affinity Chromatography Lowers Chromatography Media Costs The effect of concentrating a liquid feed sample by SPTFF on the cost of chromatography media for bind-and-elute processes was calculated for PROSEP® Ultra Plus (PUP) media (EMD Millipore), a protein A-based affinity chromatography media. The results show that the cost per gram of PUP media was significantly reduced by increasing the protein concentration in the liquid feed to about 5 g/L using SPTFF (FIG. 3).

Figure 4:
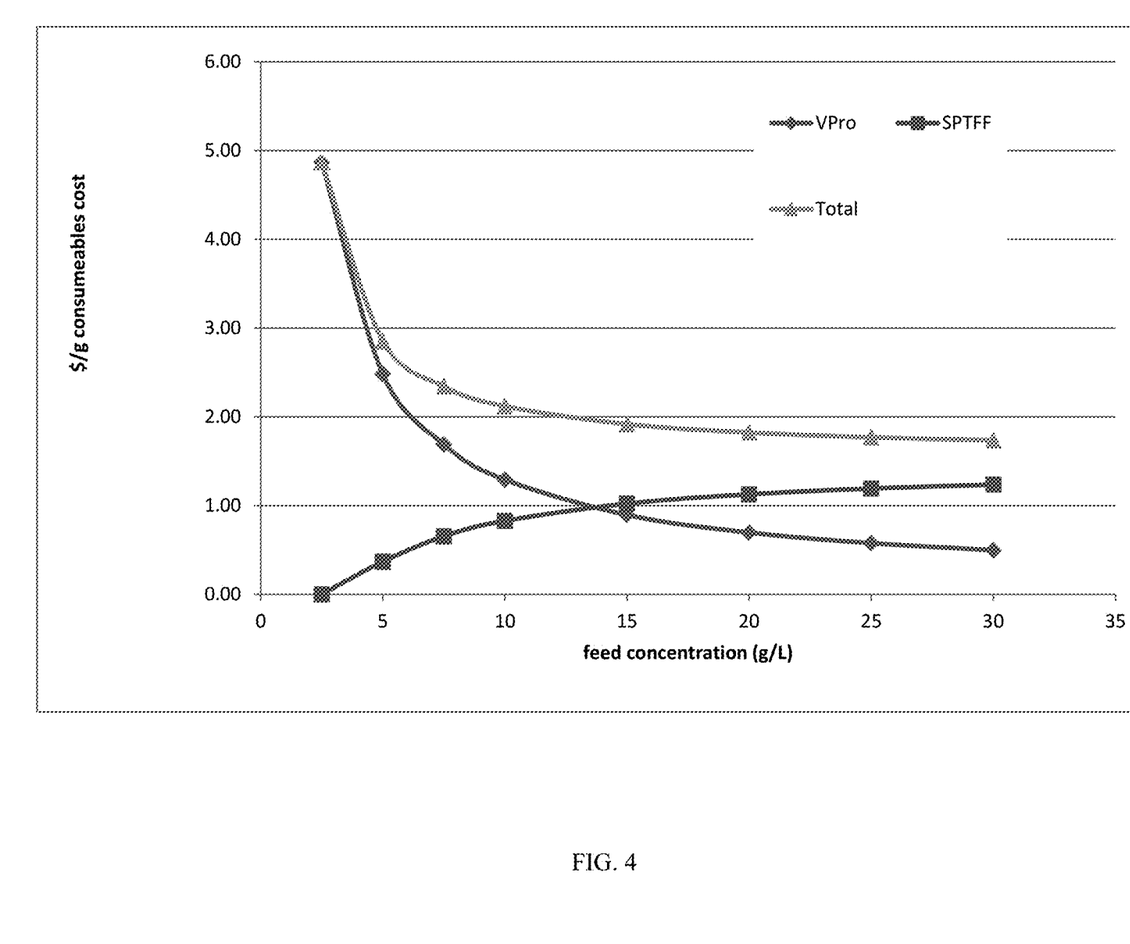
FIG. 4 is a graph plotting feed concentration in g/L against the cost of virus filters in U.S. dollars/gram of consumeable.

Example 3: Concentrating a Liquid Feed Prior to Virus Filtration Lowers Virus Filter Costs The effect of concentrating a liquid feed sample by SPTFF on the cost of non-fouling/flux-limited filters for virus filtration processes was determined. VIRESOLVE® Pro (VPro) viral filtration devices (EMD Millipore) were chosen as the virus filter. Concentrating the liquid feed prior to VPro filtration reduced both filter (VPro) costs per gram of consumeable and total costs (SPTFF+VPro) per gram of consumeable (FIG. 4). Similar results are expected for filters that are not flux-limited.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A process for purifying target proteins from non-target proteins in a liquid sample, comprising, performing in the order recited:
   a) increasing a concentration of target proteins and non-target proteins in the liquid sample by a single-pass tangential flow filtration (SPTFF) process to produce a concentrated feed having a protein concentration of 5 g/L or greater;
   b) delivering the concentrated feed to a protein A chromatography device, wherein the SPTFF process provides direct flow-through concentration of the liquid sample to the protein A chromatography device;
   c) separating the target proteins from the non-target proteins in the protein A chromatography device;
   d) recovering the target proteins from the protein A chromatography device in a recovered sample; and,
   e) determining, that the capacity of the protein A chromatography device is increased to about 10 kg to 15 kg per liter of chromatography media.

2. The process of claim 1, wherein the protein A chromatography device includes a protein A affinity resin.

3. The process of claim 1, wherein the protein A chromatography device includes a protein A affinity membrane.

4. The process of claim 1, wherein the target proteins are monoclonal antibodies.

5. The process of claim 1, wherein the non-target proteins are host cell proteins from hybridoma cells expressing the target protein.

6. The process of claim 1, wherein the liquid sample is concentrated from 1.5 times to 10 times by SPTFF to produce the concentrated feed.

7. The process of claim 1, wherein step e) comprises measuring the protein concentration of the target protein in the recovered sample.

\* \* \* \* \*